United States Patent

Anderson

(10) Patent No.: US 8,108,943 B2
(45) Date of Patent: Jan. 31, 2012

(54) METHOD AND SYSTEM FOR NEAR-FIELD SPECTROSCOPY USING TARGETED DEPOSITION OF NANOPARTICLES

(75) Inventor: Mark S. Anderson, La Crescenta, CA (US)

(73) Assignee: California Institute of Technology, Pasadena, CA (US)

( * ) Notice: Subject to any disclaimer, the term of this patent is extended or adjusted under 35 U.S.C. 154(b) by 545 days.

(21) Appl. No.: 12/324,693

(22) Filed: Nov. 26, 2008

(65) Prior Publication Data

US 2009/0249520 A1 Oct. 1, 2009

Related U.S. Application Data

(60) Provisional application No. 61/005,069, filed on Nov. 30, 2007.

(51) Int. Cl.
*G01Q 60/06* (2010.01)
(52) U.S. Cl. ........ 850/30; 850/8; 850/9; 850/17; 850/21; 850/24
(58) Field of Classification Search ............ 850/8, 9, 850/17, 21, 24, 30; 250/306, 307
See application file for complete search history.

(56) References Cited

U.S. PATENT DOCUMENTS

| | | | | |
|---|---|---|---|---|
| 6,828,786 B2* | 12/2004 | Scherer et al. | .......... | 324/300 |
| 6,850,323 B2* | 2/2005 | Anderson | .......... | 356/301 |
| 6,911,646 B1* | 6/2005 | Weitekamp | .......... | 250/234 |
| 6,987,277 B2* | 1/2006 | Baur et al. | .......... | 250/492.2 |
| 7,491,422 B2* | 2/2009 | Zhang et al. | .......... | 427/256 |
| 2002/0122873 A1* | 9/2002 | Mirkin et al. | .......... | 427/2.1 |
| 2005/0077468 A1* | 4/2005 | Baur et al. | .......... | 250/307 |
| 2005/0145021 A1* | 7/2005 | Chand et al. | .......... | 73/105 |
| 2005/0235869 A1* | 10/2005 | Cruchon-Dupeyrat et al. | .......... | 106/31.29 |
| 2005/0255237 A1* | 11/2005 | Zhang et al. | .......... | 427/180 |
| 2006/0192115 A1* | 8/2006 | Thomas et al. | .......... | 250/306 |
| 2006/0252065 A1* | 11/2006 | Zhao et al. | .......... | 435/6 |
| 2008/0019648 A1* | 1/2008 | Atwater et al. | .......... | 385/122 |
| 2009/0041404 A1* | 2/2009 | Stoddart | .......... | 385/12 |
| 2009/0162888 A1* | 6/2009 | Schmidt et al. | .......... | 435/29 |

OTHER PUBLICATIONS

Anderson, Mark S., "Nearfield surface enhanced spectroscopy using targeted nanoparticle deposition," Appl. Phys. Lett. 92, 123101 (2008).

Anderson, Mark S., et al., "A Raman-Atomic Force Microscope for Apertureless-Nearfield Spectroscopy and Optical Trapping," Review of Scientific Instruments, Mar. 1, 2002.

* cited by examiner

*Primary Examiner* — Michael Maskell

(57) ABSTRACT

There is provided in one embodiment of the invention a method for analyzing a sample material using surface enhanced spectroscopy. The method comprises the steps of imaging the sample material with an atomic force microscope (AFM) to select an area of interest for analysis, depositing nanoparticles onto the area of interest with an AFM tip, illuminating the deposited nanoparticles with a spectrometer excitation beam, and disengaging the AFM tip and acquiring a localized surface enhanced spectrum. The method may further comprise the step of using the AFM tip to modulate the spectrometer excitation beam above the deposited nanoparticles to obtain improved sensitivity data and higher spatial resolution data from the sample material. The invention further comprises in one embodiment a system for analyzing a sample material using surface enhanced spectroscopy.

17 Claims, 7 Drawing Sheets

METHOD AND SYSTEM FOR NEAR-FIELD SPECTROSCOPY USING TARGETED DEPOSITION OF NANOPARTICLES

CROSS-REFERENCE TO RELATED APPLICATION

This application is related to and claims the benefit of priority under 35 U.S.C. Section 120 to U.S. Provisional Patent Application Ser. No. 61/005,069, filed Nov. 30, 2007, which is incorporated herein by reference in its entirety.

GOVERNMENT INTERESTS

The invention described herein was made in the performance of work under a NASA contract, and is subject to the provisions of Public Law 96-517 (35 U.S.C. 202) in which the Contractor has elected to retain title.

BACKGROUND OF THE INVENTION a. Field of the Invention

The invention relates to a method and system for near-field spectroscopy using targeted deposition of nanoparticles. In particular, the invention relates to a method and system for near-field spectroscopy using targeted surface enhanced Raman scattering (SERS) and surface enhanced infrared absorption (SEIRA) localized on deposited nanoparticles from an atomic force microscope (AFM) tip.

b. Background Art

The coupling of scanning probe microscopy with vibrational spectroscopy has been driven by the need to chemically analyze nano-structured devices and materials. This has been pursued from several directions that include near-field scanning optical microscopy (NSOM) and related apertureless methods where surface enhanced Raman scattering (SERS) is localized at the tip of a scanning probe microscope. The plasmon resonance mediated SERS effect can provide extraordinary signal enhancements, and when coupled with electronic resonance, single molecule sensitivity. Known methods and systems incorporate the SERS and atomic force microscopy (AFM) using specially metalized tips with better than 50 nm (nanometer) spatial resolution. In practice, this requires the integration of the Raman spectrometer to AFM and fabrication of specialized SERS active probe tips. There are limitations due to damage or contamination of the tip and the ability to track the tip during long integration times needed for spectroscopic measurements. With tip-based Raman AFM systems and methods, high numerical aperture optics is difficult to incorporate while maintaining sample flexibility. There is also a drift in the tip position from the target during the long spectral integration times that compromise the spatial resolution. These limitations can cause increased complexity in obtaining spectrochemical information from nanometer-scale regions on a surface.

Accordingly, there is a need for a method and system for near-field spectroscopy using targeted deposition of nanoparticles that does not have the problems associated with known methods and systems.

SUMMARY OF THE INVENTION

This need for a method and system for near-field spectroscopy using targeted deposition of nanoparticles is satisfied. None of the known methods and systems provide all of the numerous advantages discussed herein. Unlike known methods and systems, embodiments of the method and system of the disclosure may provide one or more of the following advantages: the method and system provide for apertureless near-field optical spectroscopy with an atomic force microscope (AFM); the method and system do not require optical integration with the AFM tip and enable the use of fast, short working distance optics; the method and system provide for directed deposition of nanoparticles using a modified dip pen nanolithography (DPN) method that enables spectrochemical analysis with a resolution below the diffraction limit; the method and system allow the region of surface enhanced spectroscopy to be selected and focused by the arrangement of nanoparticles on the sample surface; the method and system provide for nanoparticle arrangement which determines the area of enhancement and the tuning of the plasmon resonance; the method and system do not require complex integration of a probe microscope with the spectrometer or fabrication of specialized tips; the method and system provide for near-field optical enhancement using targeted deposition of nanoparticles that may be applied to Raman, infrared or fluorescence spectroscopy; the method and system are flexible, fast, less complex, provide increased sensitivity, selectivity and spatial resolution, and provide greater surface enhancement and greater enhanced signals; the method and system provide an efficient means to obtain chemical information from a target sample material; and the method and system can be used with surface enhanced spectroscopy, such as surface enhanced Raman scattering (SERS), surface enhanced infrared absorption (SEIRA), surface enhanced fluorescence, fluorescence and infrared absorption through plasmon and phonon mediated mechanisms, and other suitable surface enhanced spectroscopy methods and techniques.

In one embodiment of the method there is provided a method for analyzing a sample material using surface enhanced spectroscopy. The method comprises the step of imaging the sample material with an atomic force microscope (AFM) to select an area of interest for analysis. The method further comprises the step of depositing nanoparticles onto the area of interest with an AFM tip. The method further comprises the step of illuminating the deposited nanoparticles with a spectrometer excitation beam. The method further comprises the step of disengaging the AFM tip and acquiring a localized surface enhanced spectrum. Optionally, the method may further comprise the step of using the AFM tip to modulate the spectrometer excitation beam above the deposited nanoparticles to obtain improved sensitivity data and higher spatial resolution data from the sample material.

In another embodiment of the method there is provided a method for analyzing a sample material using surface enhanced Raman scattering spectroscopy. The method comprises the steps of imaging the sample material with an atomic force microscope (AFM) to select an area of interest for analysis, depositing metal nanoparticles onto the area of interest with an AFM tip, illuminating the deposited nanoparticles with a Raman excitation laser, disengaging the AFM tip and acquiring a localized surface enhanced spectrum, and using the AFM tip to modulate the Raman excitation laser above the deposited nanoparticles to obtain improved sensitivity data and higher spatial resolution data from the sample material.

In another embodiment there is provided a system for analyzing a sample material using surface enhanced spectroscopy. The system comprises an atomic force microscope (AFM) optically coupled to a spectrometer for imaging the sample material to select an area of interest for analysis on the sample material. The system further comprises an AFM tip for depositing metal nanoparticles onto the area of interest on the sample material. The system further comprises a spectrometer excitation beam for illuminating the deposited nanoparticles and acquiring a localized surface enhanced spectrum when the AFM tip is disengaged.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION OF THE INVENTION

Disclosed embodiments will now be described more fully hereinafter with reference to the accompanying drawings, in which some, but not all disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

The disclosure provides for a method and system for near-field spectroscopy using targeted deposition of nanoparticles. In particular, the invention relates to a method and system for near-field spectroscopy using targeted surface enhanced Raman scattering (SERS) deposition of nanoparticles from an atomic force microscope (AFM) tip. However, other surface enhanced spectroscopy, such as surface enhanced infrared absorption (SEIRA), surface enhanced fluorescence, fluorescence and infrared absorption through plasmon and phonon mediated mechanisms, and other suitable surface enhanced spectroscopy methods may also be used. Accordingly, one of ordinary skill in the art will recognize and appreciate that the method and system of the disclosure can be used in any number of applications various surface enhanced spectroscopy methods.

Figure 1:
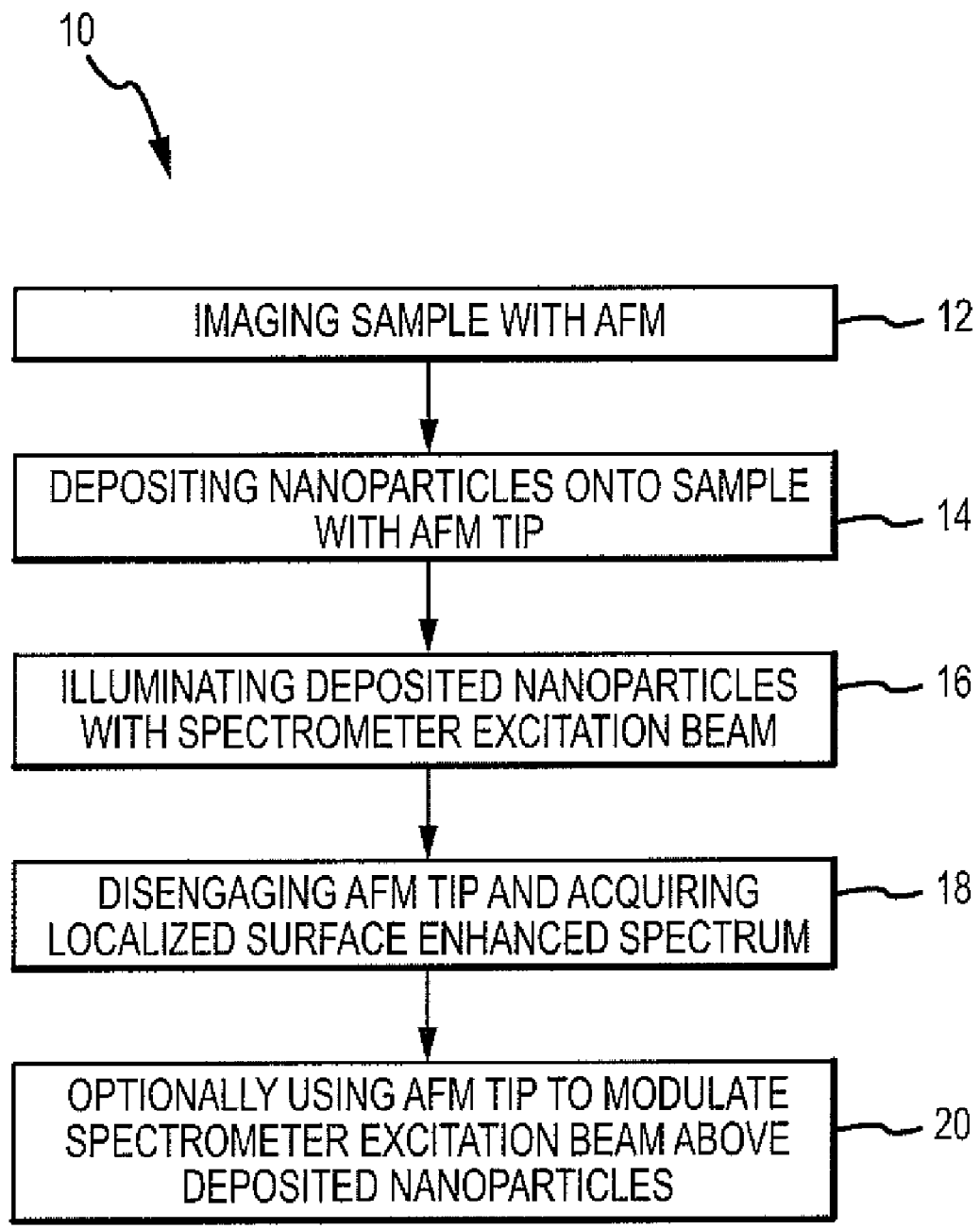
FIG. 1 is a flow diagram of one of the embodiments of the method of the invention.

Referring now to the drawings, FIG. 1 is a flow diagram of one of the embodiments of a method 10 for analyzing a sample material using surface enhanced spectroscopy, The surface enhanced spectroscopy may comprise surface enhanced Raman scattering (SERS), surface enhanced infrared absorption (SEIRA), surface enhanced fluorescence, fluorescence and infrared absorption through plasmon and phonon mediated mechanisms, or another suitable surface enhanced spectroscopy method or technique. Preferably, the surface enhanced spectroscopy is SERS. The sample material may comprise a biological material, biomolecules, a thin film, an in situ sample, a microdevice, an electronic integrated circuit and memory device, or another suitable sample material. The method may also use relatively thick and opaque samples.

Figure 2:
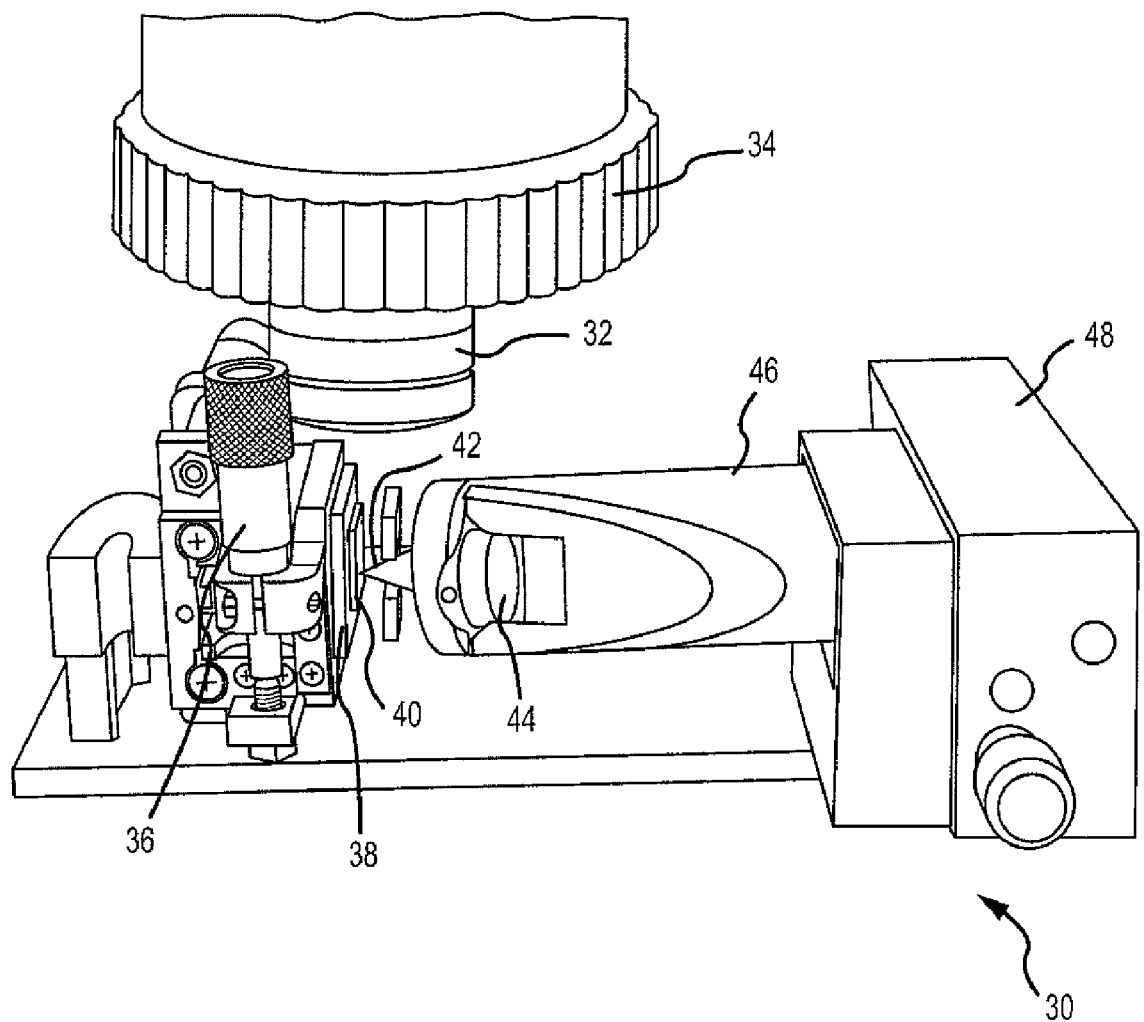
FIG. 2 is a front perspective view of an embodiment of a Raman atomic force microscope (AFM) that may be used with the method of the invention.

The method 10 comprises step 12 of imaging a sample material with an atomic force microscope (AFM) to select an area of interest for analysis, such as for high resolution spectrochemical analysis. Phase contrast or friction contrast AFM imaging modes may be used to reveal surface chemistry variation and boundaries. This qualitative information may be used to guide the spectroscopic analysis. The AFM may comprise a Raman AFM or another suitable scanning probe microscope. FIG. 2 is a front perspective view of an embodiment of a Raman atomic force microscope (AFM) 30 that may be used with the method of the invention. The AFM 30 may comprise an objective 32, a spectrometer element 34, an x-y-z stage 36, a substrate 38, a sample element 40, an AFM tip 42, a viewing mirror 44, an AFM scan tube 46, and an AFM support element 48. The laser and laser or excitation beam are not shown in FIG. 2. However, the laser or excitation beam travels through the objective 32 of the spectrometer element 34 or optical microscope onto sample material.

Figure 3:
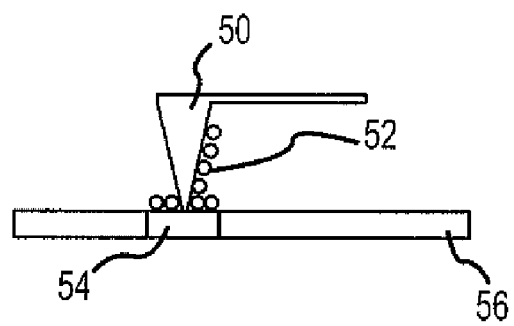
FIG. 3 is a front view of a Raman AFM tip depositing nanoparticles onto a sample.
Figure 6:
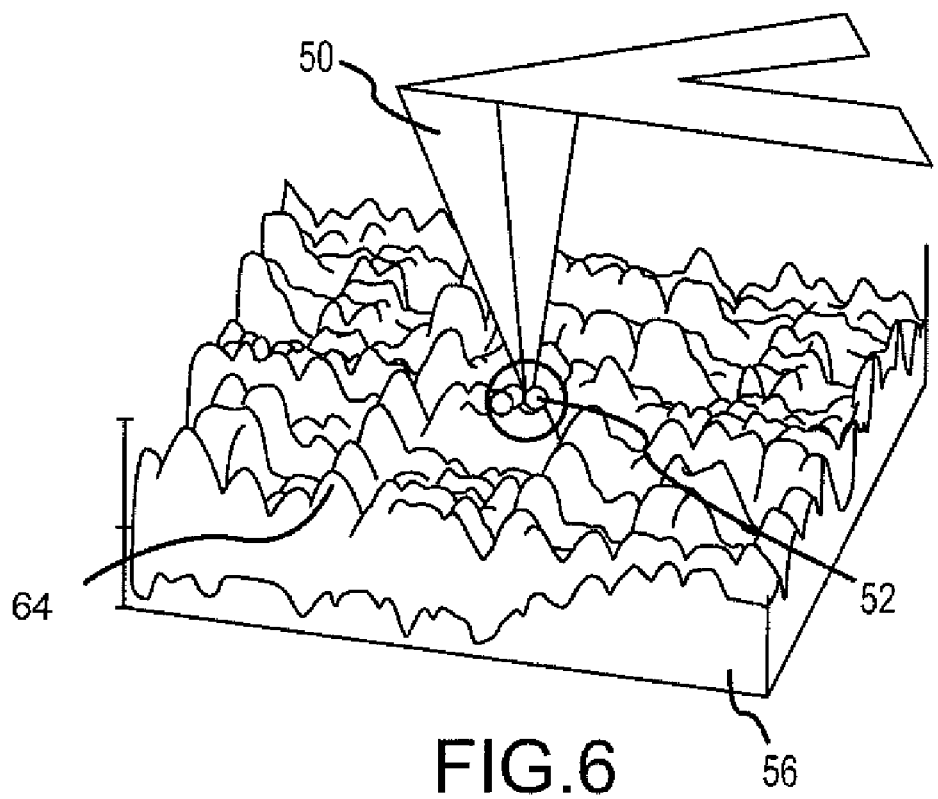
FIG. 6 is a front perspective view of a Raman AFM tip depositing nanoparticles onto a sample and showing topographic images of areas of interest.

The method 10 further comprises step 14 of depositing nanoparticles onto the area of interest of the sample material with an AFM tip. The nanoparticles preferably comprise a metal such as gold, silver, copper, platinum, and mixtures thereof, or another suitable metal or mixture of metals. More preferably, the nanoparticles comprise gold or silver. The nanoparticles may also comprise dielectric particles. Localized SERS or SEIRA areas of interest or active regions are fabricated directly on a surface of the sample by depositing nanoparticles from an AFM tip. The method uses a similar methodology to a modified dip pen nanolithography (DPN) methodology. Preferably, the AFM tip is dipped into a colloidal gold solution and a single particle or particle cluster is deposited onto the area of interest or the selected region. The precursors of the nanoparticles may be deposited using DPN techniques. The photoreduction of silver chloride and gold salts and gold salt solutions may be used to create SERS active surfaces. The advantage of using liquid solution deposited precursors lies in the DPN control and precision of deposition. FIG. 3 is a front view of a Raman AFM tip 50 depositing nanoparticles 52 onto a sample surface 54 attached to substrate 56. Preferably, the AFM tip deposits gold nanoparticles on the sample surface from a colloidal solution. FIG. 6 is a front perspective view of the Raman AFM tip 50 depositing nanoparticles 52 onto the sample and showing topographic images 64 of areas of interest. The need for high accuracy placement may be mitigated simply by imaging after particle deposition. The AFM may then reimage the surface to establish a precise location of the deposited particles on the sample surface. Preferably, the AFM has a closed loop head and provides good placement reproducibility. However, the need for placement accuracy is mitigated simply by imaging after particle deposition. The AFM may then establish a very precise location of the deposited particles on the sample surface.

The SERS effect has been explained as having both resonant and non-resonant field enhancement due to the metallization of the tip as well as an additional chemical enhancement that helps explain the extraordinary amplification of the Raman signals. The SERS enhancement is maximized when the metal nanoparticles or grains are smaller than the incident laser wavelength, the metal has the optical properties to generate surface plasmons, and the analyte molecules have matching optical properties to couple to the plasmon field. The greatest enhancements are observed with silver, gold, copper, and platinum with grain diameters between 10 and 200 nm. SERS active AFM tips ideally should have the properties of SERS particles. The SERS-AFM tips are preferably fabricated by simple plasma deposition of gold or silver (grain size of approximately 40 nanometers) on to the silicon tip.

Figure 4:
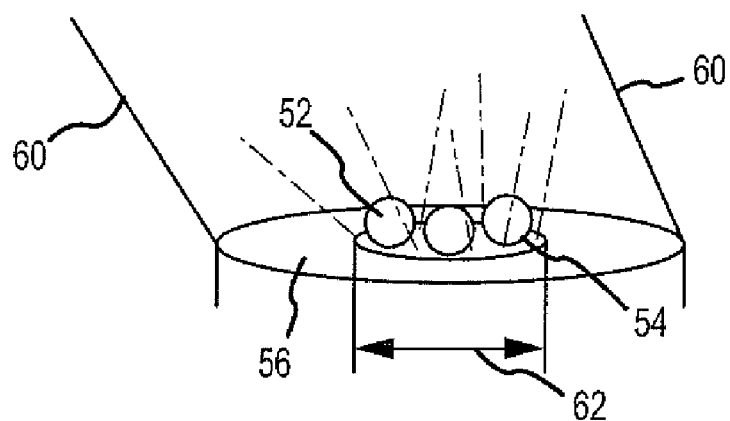
FIG. 4 is a front perspective view showing illumination of deposited nanoparticles in a spectrometer excitation beam and spectrum acquisition.
Figure 7:
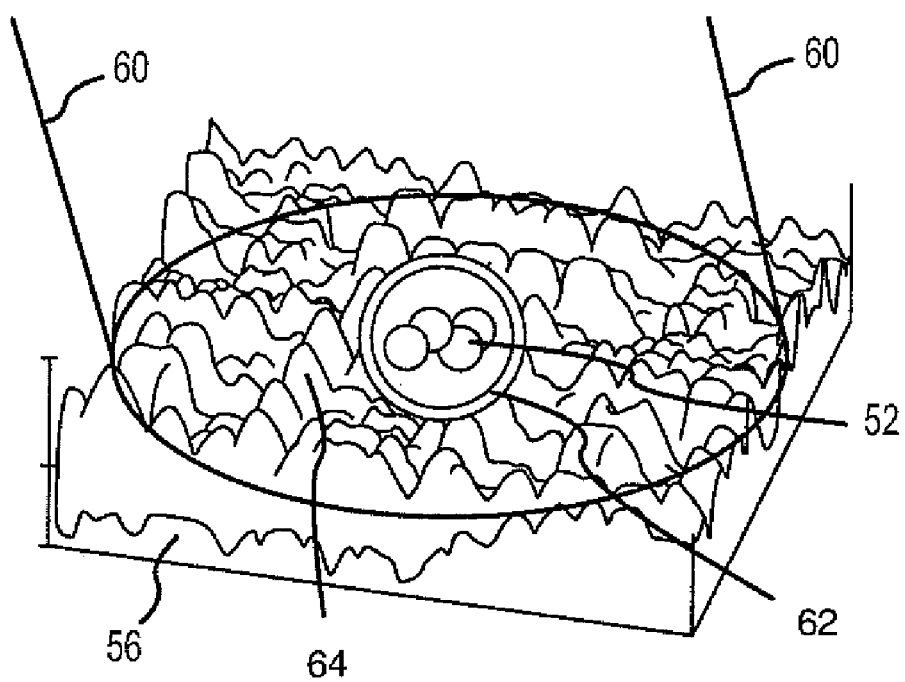
FIG. 7 is a front perspective view showing illumination of deposited nanoparticles in a spectrometer excitation beam, showing the region of enhanced spectroscopy and showing topographic images of areas of interest.
Figure 10:
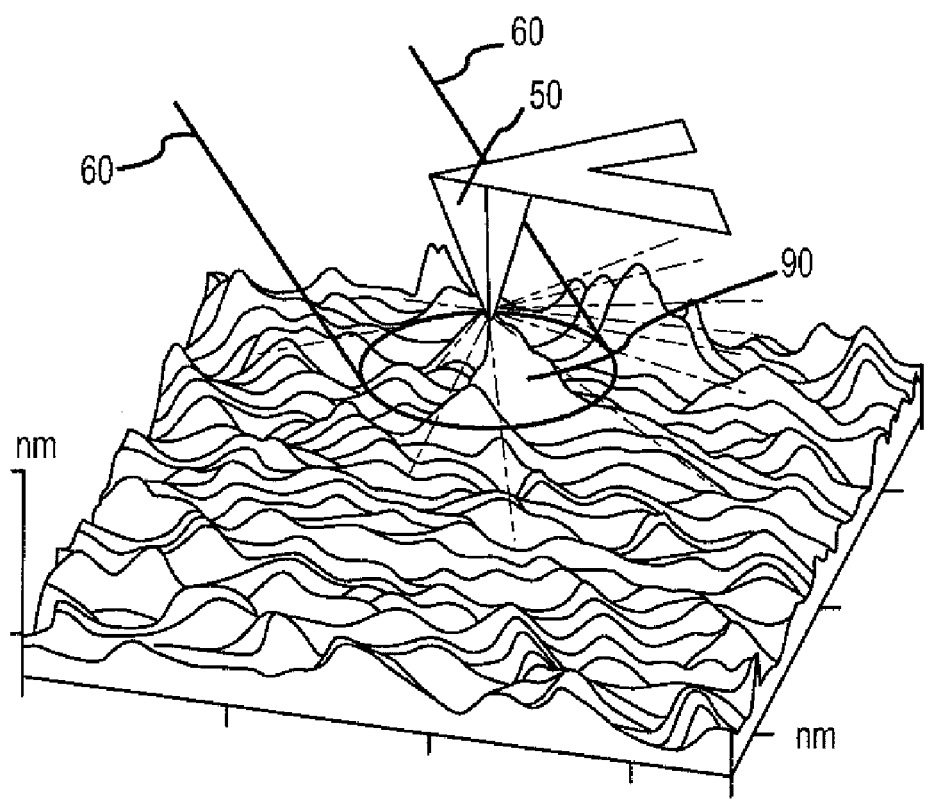
FIG. 10 is a front perspective view showing local enhancement of a Raman signal at the AFM tip.
Figure 11:
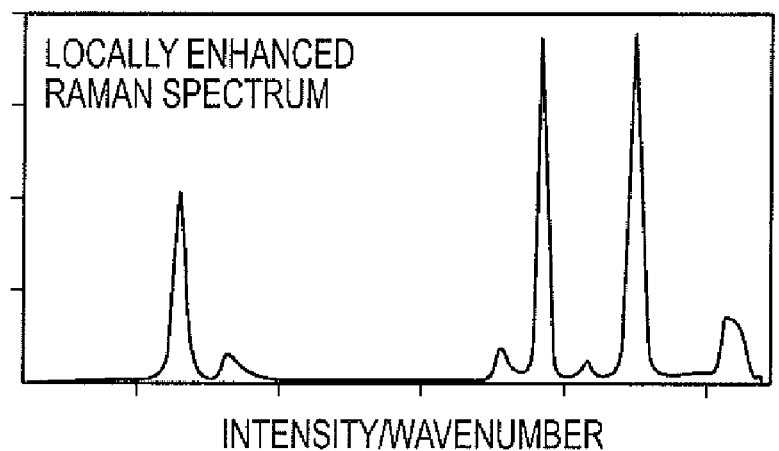
FIG. 11 is a graphical representation of a SERS Raman spectra of the area of local enhancement of FIG. 10.

The method 10 further comprises step 16 of illuminating the deposited nanoparticles with a spectrometer excitation beam. The spectrometer excitation beam may comprise a Raman excitation laser beam, an infrared laser beam, or another suitable spectrometer excitation beam. FIG. 4 is a front perspective view showing illumination of deposited nanoparticles 52 on the sample surface 54 of the substrate 56 in a spectrometer excitation beam 60 and an enhanced signal region 62 of which the locally enhanced spectrum is acquired. FIG. 7 is a front perspective view showing illumination of deposited nanoparticles 52 in the spectrometer excitation beam 60, showing enhanced signal region 62 of enhanced spectroscopy and showing topographic images 64 of areas of interest. FIG. 10 is a front perspective view showing local enhancement 90 of a Raman signal at the Raman AFM tip 50 illuminated by the spectrometer excitation beam 60. FIG. 11 is a graphical representation of a SERS Raman spectra of the area of local enhancement 90 of FIG. 10. The illuminating step does not require the integration of the AFM and the spectrometer when the sample area is properly registered to the spectrometer excitation beam, such as the Raman excitation beam. Raman microprobes have beam spots sized in approximately the 1-10 micron range, so sample registration is possible using the optical microscopes on the AFM and a Raman microprobe. For SERS applications, the illuminating step may further comprise illuminating the sample and AFM tip with at least quasi-monochromatic light in the Raman spectrometer from a side direction approximately perpendicular to an imaginary line connecting the tip and the sample. The light source is focused in the near field of the tip.

The method 10 further comprises step 18 of disengaging the AFM tip and acquiring a localized surface enhanced spectrum. The localized surface enhanced spectrum is preferably enhanced over ten (10) times as compared to enhancement with conventional spectroscopy methods.

Figure 5:
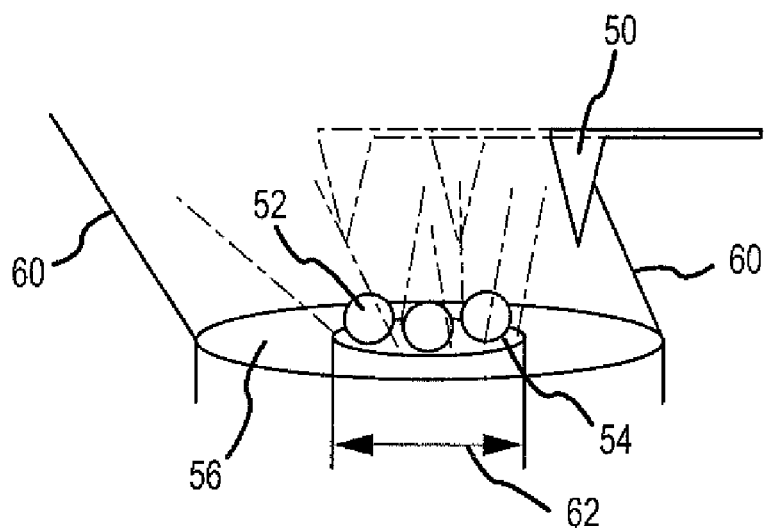
FIG. 5 is a front perspective view showing a Raman AFM tip modulating the spectrometer excitation beam above the deposited nanoparticles.

Optionally, the method 10 may further comprise step 20 of using the AFM tip to modulate the spectrometer excitation beam above the deposited nanoparticles to determine a more precise location and orientation of the nanoparticles to the sample surface or to obtain improved sensitivity data and higher spatial resolution data from the sample material. FIG. 5 is a front perspective view showing the Raman AFM tip 50 modulating the spectrometer excitation beam 60 above the deposited nanoparticles 52 and on the sample surface 54 of the substrate 56 and above the enhanced signal region 62. Thus, the AFM tip 50 or cantilever moves back and forth over the nanoparticles 52 and the enhanced signal region 62 to modulate the spectrometer excitation beam 60 by serving as a local shutter above the enhanced particle region. This can improve discrimination of the enhanced signal from areas away from the particles but still illuminated inside the beam. The AFM tip or cantilever may be used to modulate the beam by serving as a microshutter above the deposited nanoparticles to locally modulate the spectrometer excitation beam for improved sensitivity and discrimination from samples with a background signal.

The method uses tipless near-field microscopy and builds on established methods in DPN, surface enhanced Raman scattering (SERS), and surface enhanced infrared absorption (SEIRA), and may be applied to surface enhanced fluorescence or other suitable methods. In addition, DPN methods may be used for the patterning of nanometer structures on surfaces. The use of DPN techniques provides a range of size scales for enhanced spectroscopy. The structures that guide the surface plasmon resonance may be used and patterned in a variety of geometries to tailor the frequency response and position of the field enhancement. The tipless near-field scanning optical microscopy (NSOM) method may be a useful tool to characterize a wide range of nanometer scale devices and materials. The method enables the detailed study of surfaces by providing spectrochemical information for future nanoelectronics and material applications.

In another embodiment there is provided a system for analyzing a sample material using surface enhanced spectroscopy. The system may be portable. The system comprises an atomic force microscope (AFM) (see FIG. 2, reference number 30) optically coupled to a spectrometer (see FIG. 2, reference number 34) for imaging sample material (see FIG. 3, reference number 54) to select an area of interest for analysis on the sample material. The system further comprises an AFM tip (see FIG. 3, reference number 50) for depositing metal nanoparticles (see FIG. 3, reference number 52) onto the area of interest on the sample material. The system further comprises a spectrometer excitation beam (see FIG. 4, reference number 60) for illuminating the deposited nanoparticles and acquiring a localized surface enhanced spectrum (see FIG. 4, reference number 62) when the AFM tip is disengaged. The surface enhanced spectroscopy may comprise surface enhanced Raman scattering (SERS), surface enhanced infrared absorption (SEIRA), surface enhanced fluorescence, fluorescence and infrared absorption through plasmon and phonon mediated mechanisms, or another suitable surface enhanced spectroscopy method or technique. The sample material may comprise a biological material, biomolecules, a thin film, an in situ sample, a microdevice, an electronic integrated circuit and memory device, or another suitable sample material. The nanoparticles preferably comprise a metal such as gold, silver, copper, platinum, and mixtures thereof, or another suitable metal or mixture of metals. More preferably, the nanoparticles comprise gold or silver. The metal nanoparticles may be deposited with a modified dip pen nanolithography (DPN) methodology. The spectrometer excitation beam may comprise a Raman excitation laser beam, an infrared laser beam, or another suitable spectrometer excitation beam.

EXAMPLES

The following examples are offered by way of illustration and not by way of limitation. Experiments were conducted using various embodiments of the disclosed method. A commercial AFM (Nanoscope 4/3200 obtained from Digital Instruments of Santa Barbara, Calif.) and a Raman spectrometer equipped with a microscope attachment (Holoprobe, 785 nm (nanometer) Laser, from Kaiser Optical Systems of Ann Arbor, Mich.) were used. The Raman microprobe preferably used a 50× lens with a 0.75 numerical aperture (NA) and 200 second (s) acquisition time. The excitation laser was preferably at a 785 nm (nanometer) wavelength.

Example 1

The first test sample was a thin film molecular layer of trans-1,2 bis-(4-pyridyl)ethylene (BPE) (Sigma-Aldrich) coating a quartz slide. The BPE film was cast from a dilute methanol solution using a droplet evaporation procedure developed for testing SERS substrates. The film could not be detected using conventional Raman scattering and was estimated to be approximately one to two molecular layers based on the grazing angle infrared reflectance spectrum. A gold nanoparticle solution (40 or 60 nm (nanometer), colloidal gold solution, obtained from Ted Pella of Redding, Calif.) was collected on a silicon AFM tip-cantilever and then deposited on the surface of the sample. The collection was made by engaging the AFM tip in contact mode to a drop of colloidal solution that was evaporated to approximately 50% of its original volume. The collection time was approximately one (1) second (s). Deposition was made immediately after collection of the gold nanoparticle solution by engaging the AFM to the sample surface. Engaging to the sample on a very small scan size (one (1) nm (nanometer)) followed by immediate withdrawal resulted in deposition of a small number or single particles. Engaging and scanning with larger 200 nm (nanometer) scan sizes resulted in clusters of particles being deposited. After particle deposition, the colloidal solution remaining on the AFM cantilever and sample surface was allowed to dry for several minutes.

The Raman feasibility test examined the surface enhanced Raman spectra from gold nanoparticles deposited on BPE coated surfaces. Once the gold particle(s) were deposited on BPE coated quartz surface, the surface was then imaged using the AFM. Gold particles were chosen on the basis of availability and stability. However, silver and other metal colloids are SERS active and may also be used. Silver may provide good enhancement. The same tip was used to deposit the particles and to image the surface. The used tip was not adversely affected and produced reasonable images.

Figure 8:
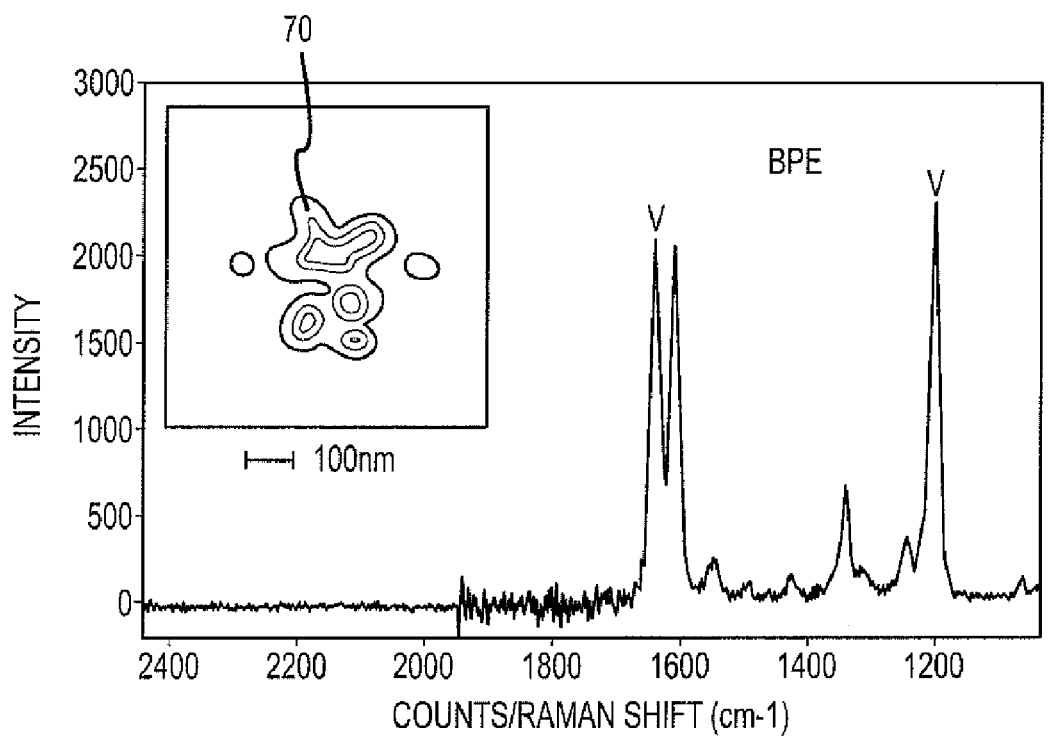
FIG. 8 shows SERS Raman spectra of a thin BPE film on a quartz surface from a deposited ten particle cluster with an insert diagram of the AFM image.

FIG. 8 shows SERS Raman spectra of the thin BPE film on the quartz surface from the deposited ten particle cluster with an insert diagram 70 of the AFM image acquired. The enhanced area is approximately 250 nm (nanometer) in diameter and that is well below the diffraction limit of the 785 nm (nanometer) Raman excitation laser.

Figure 9:
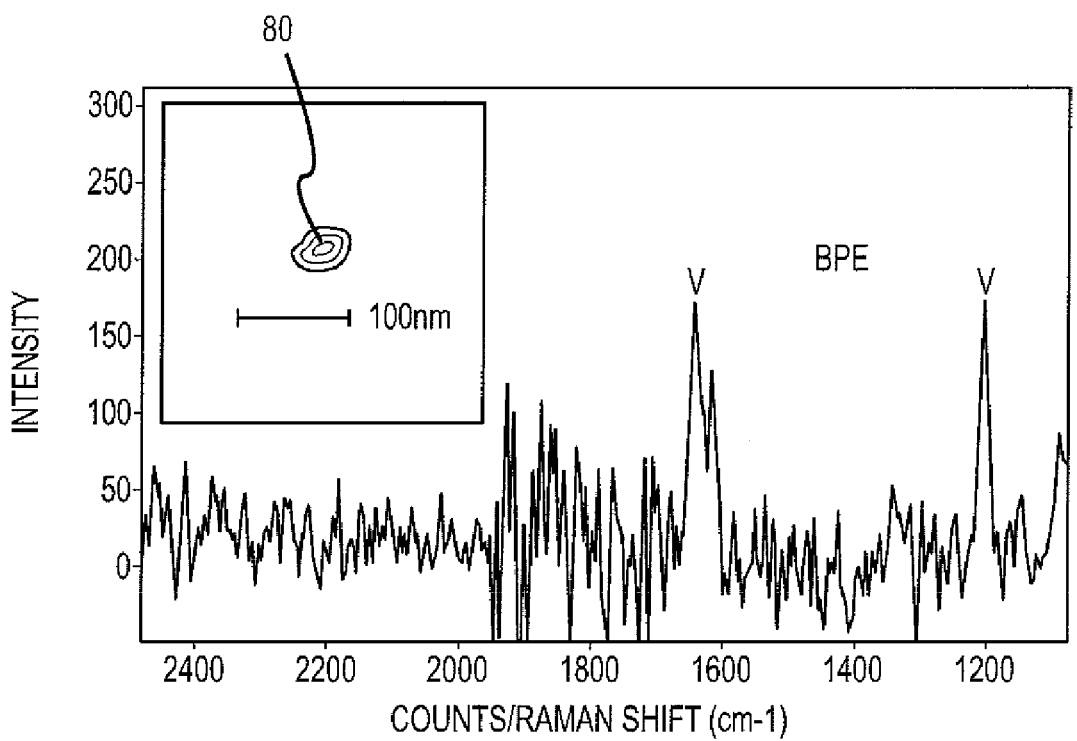
FIG. 9 shows SERS Raman spectrum of a thin BPE film on a quartz surface from a deposited 40 nm (nanometer) particle with an insert diagram of the AFM image.

FIG. 9 shows SERS Raman spectrum of the thin BPE film on the quartz surface from a deposited 40 nm (nanometer) diameter particle with an insert diagram 80 the AFM image acquired. The detection of the weak signal from the small areas was facilitated by the high numerical aperture optics and the relatively long 200 second Raman acquisition time.

The Raman excitation laser had an angle of incidence and collection that was determined by the lens (0.75 NA). The thin BPE films were not detectable by conventional Raman spectroscopy in regions without the gold nanoparticles. No BPE was detectable on this surface before the particles were deposited.

Example 2

Localized SEIRA was tested using 60 nm (nanometer) colloidal gold similarly deposited from the AFM tip onto a silicone (DC200 polydimethyl siloxane, obtained from Dow Corning of Midland, Mich.) coated substrate. The film was cast from a dilute dichloromethane solution onto a polished silicon wafer. The measurement was made using a Varian/Digilab FTS 6000 Fourier transform infrared (FTIR) microscope with a UMA 600 microscope. The FTIR microscope was equipped with a liquid nitrogen cooled, narrow band, mercury cadmium telluride detector. The nanoparticle area was imaged by AFM after deposition. The location was registered by scribing or marking on the silicon substrate for the FTIR microscope. The far field illuminated area was 20×20 micron as set by the FTIR microscope aperture mask.

Figure 12:
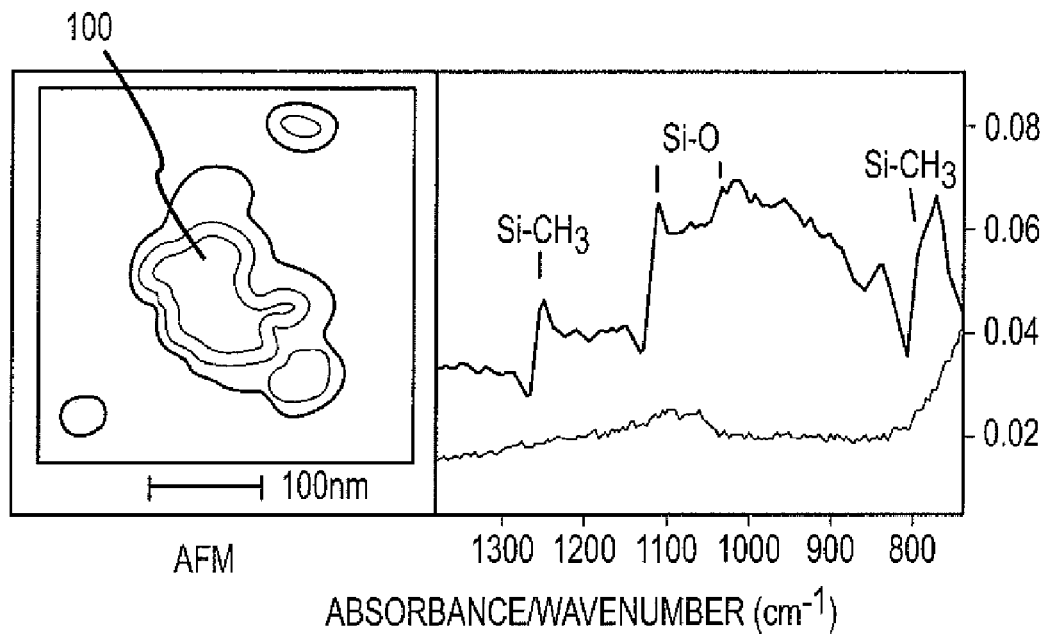
FIG. 12 shows FTIR (Fourier transform infrared) microscope spectra of a cluster of AFM deposited gold nanoparticles on a thin silicone film with an insert diagram of the AFM image; and, FIG. 13 shows a side view from an optical microscope of a Raman AFM showing a laser illuminated diamond particle collected on the SERS-AFM tip, and shows the SERS spectra compared to a conventional Raman spectra of the diamond particle on glass without enhancement.

A similar result was demonstrated for SEIRA using 60 nm (nanometer) diameter gold nanoparticles deposited onto a thin silicone coated silicon wafer. FIG. 12 shows FTIR (Fourier transform infrared) microscope spectra of a cluster of AFM deposited gold nanoparticles on a thin silicone film with an insert diagram 100 of the AFM image. The enhanced area was approximately 200 nm in diameter as shown in the corresponding AFM image. For comparison, the unenhanced film on an adjacent region is not detectable as shown in the bottom spectrum. The unenhanced silicone coated region in proximity to the enhanced region serves as a control. The peak shape is altered somewhat having a tailing, derivative-like appearance. The enhanced region was estimated to be within a diameter of approximately 200 nanometers or less. This was well below the mid-infrared diffraction limit of approximately 10 micron. The enhancement factor for SEIRA was generally less than for SERS. However, except for a limited subset of highly enhancing compounds, SEIRA had comparable sensitivity to SERS. This was a result of higher infrared cross section than Raman.

The results showed that the targeted placement of gold nanoparticles may be used to locally enhance the Raman and infrared signal of the sample surface. Theoretical and experimental work indicated that the field enhancement was mainly within 5 nm (nanometer) from the particle surface. The particle surface roughness and interactions with other particles modified the enhanced field orientation, strength, and the plasmon resonance frequency. These parameters may be used to further localize and control the surface enhanced spectroscopy. This analysis revealed how the placement of particles may be used to guide and focus enhanced signal onto the sample area of interest.

Figure 13:
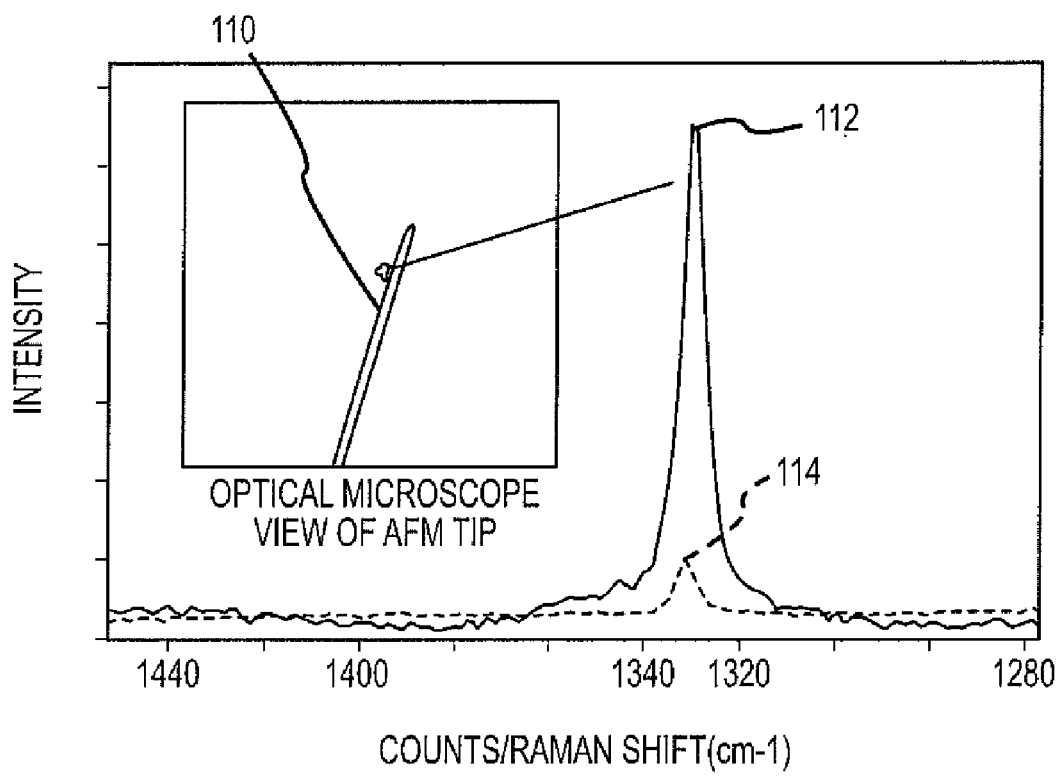

FIG. 13 shows a side view from an optical microscope of a Raman AFM showing a laser illuminated diamond particle collected on the SERS-AFM tip, and shows the SERS spectra 112 compared to a conventional Raman spectra 114 of the diamond particle on glass without enhancement.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting. Although specific terms are employed herein, they are used in a generic and descriptive sense only and not for purposes of limitation.

What is claimed is:

1. A method for analyzing a sample material using surface enhanced spectroscopy comprising the steps of:
    imaging the sample material with an atomic force microscope (AFM) to select an area of interest for analysis;
    depositing nanoparticles onto the area of interest with an AFM tip;
    illuminating the deposited nanoparticles with a spectrometer excitation beam separate from the AFM tip; obtaining from the sample material a precise location of the deposited nanoparticles on the sample material using the AFM tip; and,
    disengaging the AFM tip and acquiring a localized surface enhanced spectrum,
    wherein the localized surface enhanced spectrum is enhanced over 10 times by depositing the nanoparticles onto the area of interest with the AFM tip, as compared to without depositing the nanoparticles onto the area of interest.

2. The method of claim 1 further comprising the step after the disengaging step of using the AFM tip to modulate the spectrometer excitation beam above the deposited nanoparticles to obtain improved sensitivity data and higher spatial resolution data from the sample material.

3. The method of claim 1 wherein the surface enhanced spectroscopy is selected from the group comprising surface enhanced Raman scattering (SERS), surface enhanced infrared absorption (SEIRA), surface enhanced fluorescence, and fluorescence and infrared absorption through plasmon and phonon mediated mechanisms.

4. The method of claim 1 wherein the sample material is a material selected from the group comprising a biological material, biomolecules, a thin film, an in situ sample, a microdevice, and an electronic integrated circuit and memory device.

5. The method of claim 1 wherein the nanoparticles comprise a metal selected from the group comprising gold, silver, copper, platinum, and mixtures thereof.

6. The method of claim 1 wherein the spectrometer excitation beam is selected from the group comprising a Raman excitation laser beam and an infrared laser beam.

7. The method of claim 1 wherein the surface enhanced spectroscopy surface is enhanced Raman scattering (SERS) and the illuminating step further comprises illuminating the sample and AFM tip with at least quasi-monochromatic light in the Raman spectrometer from a side direction approximately perpendicular to an imaginary line connecting the tip and the sample.

8. A method for analyzing a sample material using surface enhanced Raman scattering spectroscopy comprising the steps of:
    imaging the sample material with an atomic force microscope (AFM) to select an area of interest for analysis;
    depositing metal nanoparticles onto the area of interest with an AFM tip;
    illuminating the deposited nanoparticles with a Raman excitation laser that is separate from the AFM tip; obtaining from the sample material a precise location of the deposited metal nanoparticles on the sample material;
    disengaging the AFM tip and acquiring a localized surface enhanced spectrum; and,
    using the AFM tip to modulate the Raman excitation laser above the deposited nanoparticles to obtain improved sensitivity data and higher spatial resolution data from the sample material,
    wherein the localized surface enhanced spectrum is enhanced over 10 times by depositing the metal nanoparticles onto the area of interest with the AFM tip, as compared to without depositing the metal nanoparticles onto the area of interest.

9. The method of claim 8 wherein the sample material is a material selected from the group comprising a biological material, biomolecules, a thin film, an in situ sample, a microdevice, and an electronic integrated circuit and memory device.

10. The method of claim 8 wherein the metal nanoparticles comprise a metal selected from the group comprising gold, silver, copper, platinum, and mixtures thereof.

11. A system for analyzing a sample material using surface enhanced spectroscopy comprising:
    an atomic force microscope (AFM) optically coupled to a spectrometer for imaging the sample material to select an area of interest for analysis on the sample material;
    an AFM tip for depositing metal nanoparticles onto the area of interest on the sample material and configured to obtain a precise location of the deposited metal nanoparticles on the sample material; and,
    a spectrometer excitation beam separate from the AFM tip for illuminating the deposited nanoparticles and acquiring a localized surface enhanced spectrum when the AFM tip is disengaged,
    wherein the localized surface enhanced spectrum is enhanced over 10 times by depositing the metal nanoparticles onto the area of interest on the sample material with the AFM tip, as compared to without depositing the metal nanoparticles onto the area of interest on the sample material.

12. The system of claim 11 wherein the surface enhanced spectroscopy is selected from the group comprising surface enhanced Raman scattering (SERS), surface enhanced infrared absorption (SEIRA), surface enhanced fluorescence, and fluorescence and infrared absorption through plasmon and phonon mediated mechanisms.

13. The system of claim 11 wherein the sample material is a material selected from the group comprising a biological material, biomolecules, a thin film, an in situ sample, a microdevice, and an electronic integrated circuit and memory device.

14. The system of claim 11 wherein the metal nanoparticles comprise a metal selected from the group comprising gold, silver, copper, platinum, and mixtures thereof.

15. The system of claim 11 wherein the spectrometer excitation beam is selected from the group comprising a Raman excitation laser beam and an infrared laser beam.

16. The system of claim 11 wherein the surface enhanced spectroscopy is surface enhanced Raman scattering (SERS).

17. The system of claim 11 wherein the metal nanoparticles are deposited with a modified dip pen nanolithography (DPN).

* * * * *